United States Patent [19]

Klein

[11] Patent Number: 4,590,929

[45] Date of Patent: May 27, 1986

[54] TOOLS FOR ORTHOPAEDIC SURGERY AND THE LIKE

[76] Inventor: Harvey A. Klein, 1000-E. 19th St., Brooklyn, N.Y. 11230

[21] Appl. No.: 491,244

[22] Filed: May 3, 1983

[51] Int. Cl.$^4$ .......................... A61F 5/04; B23B 51/00
[52] U.S. Cl. ............................... 128/92 E; 128/92 R; 128/305; 128/92 EB; 408/224; 408/225
[58] Field of Search ............... 128/92 R, 92 EB, 305, 128/92 E; 408/82, 223–225, 230, 214, 211

[56] References Cited

U.S. PATENT DOCUMENTS

| | | | |
|---|---|---|---|
| 252,704 | 1/1882 | Southwick | 408/223 |
| 370,484 | 9/1887 | Latham | 408/225 |
| 1,471,866 | 10/1923 | Simpson | 408/224 |
| 2,264,922 | 12/1941 | Van Hooser | 408/224 |
| 2,705,515 | 4/1955 | Walker | 408/224 |
| 4,116,200 | 9/1978 | Braun et al. | 128/305 |
| 4,265,231 | 5/1981 | Scheller, Jr. et al. | 128/92 EB |
| 4,312,337 | 1/1982 | Donohue | 128/92 EB |
| 4,330,229 | 5/1982 | Croydon | 408/230 |

FOREIGN PATENT DOCUMENTS 25718 of 1913 United Kingdom ................ 408/224

Primary Examiner—Gene Mancene
Assistant Examiner—C. W. Shedd
Attorney, Agent, or Firm—Israel Nissenbaum

[57] ABSTRACT

A method for reducing the incidence of wire breakage in orthopaedic surgery wherein said wire passes through apertures drilled in bone fragments for effecting a wire connection therebetween during healing. Said method comprises removing stress raising corners or edges, caused by the formation of said apertures, from positions in said bone fragments which are in contact with said wire. Manipulation of an aperturing drill or the utilization of novel radius cutters is utilized in effecting removal of said stress raising edges. The novel rotating radius cutters comprise arcuate cutting surfaces and integral drill or aperture positioning means.

10 Claims, 11 Drawing Figures

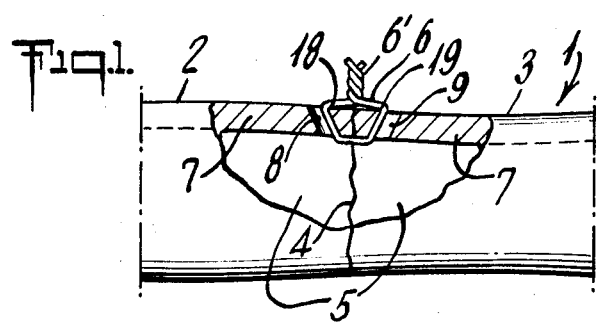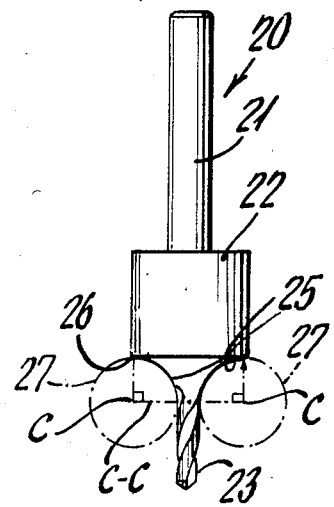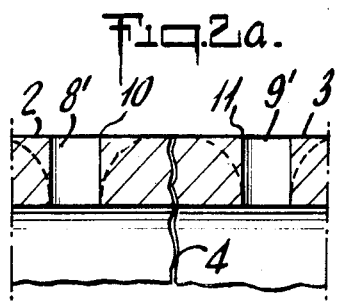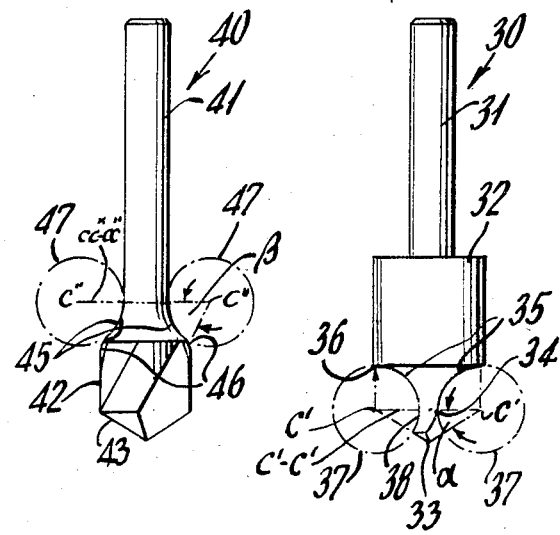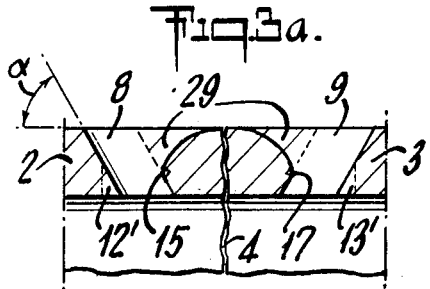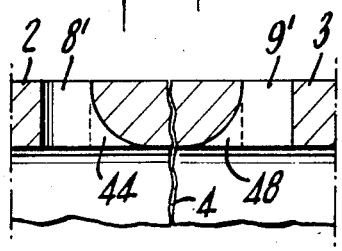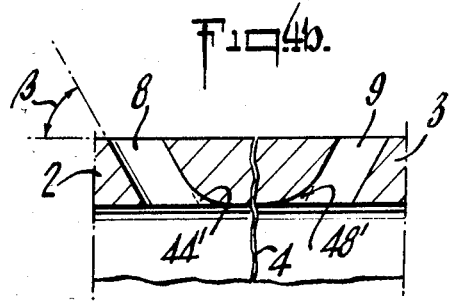

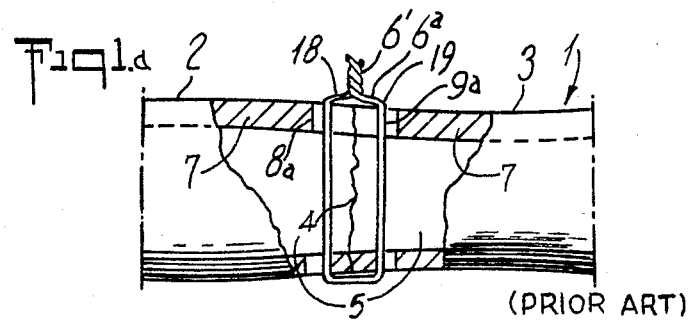
Fig 1.d (PRIOR ART)
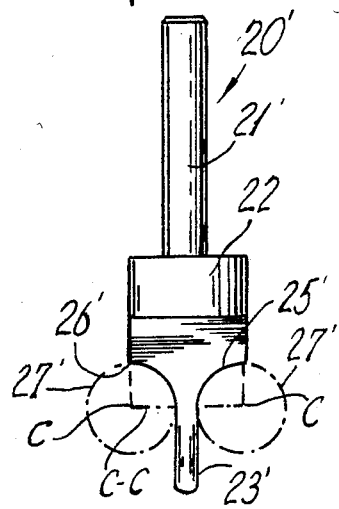
Fig 2'

TOOLS FOR ORTHOPAEDIC SURGERY AND THE LIKE

This invention relates to methods for connecting bone fragments during healing and particularly to orthopaedic methods involving twisted wire connections.

When open reduction and internal fixation are indicated, bone fragments are commonly held together by twisted wire connections during the period of time required for the knitting together of the bone fragments. The procedure involved in effecting such twisted wire connection comprises the drilling of apertures into each of the bone fragments in abutting adjacent areas on either side of the break or fracture. Such apertures are generally made by a common twist drill through the cortex of the bone fragments and into the medullary canal or continuing through both cortices. Surgical wire, commonly of stainless stell, is introduced into one of the apertures, optionally by guide means and is moved through the medullary canal and across the fracture site (or break) and is thereafter pulled out of the other aperture. Alternatively, the wire is passed completely through one of the bone fragments through apertures drilled through both cortices across the bone diameter. The wire is then guided for reinsertion and return through apertures drilled completely through the other bone fragment. The wire ends are then tightened and twisted together to maintain the bones in proper position for healing. It has been discovered however, that a significant portion of such twisted wire connections break either during the healing period of about six weeks or after healing has taken place. In the former instance, wire breakage prior to healing may result in improper alignment and/or weakened healing of the bone fragments. In the latter instance, wire breakage at any time results in exposed sharp wire ends in a patient's body with concomitant patient pain thereby necessitating surgical removal thereof.

It is an object of the present invention to provide a method for reducing the incidence of breakage of wires utilized in the connection of bone fragments particularly in orthopaedic surgery.

It is a further object of the present invention to provide novel tools for effecting such method.

These and other objects, features and advantages of the present invention will become more evident from the following discussion as well as the drawings in which:

FIGS. 1 and 1a are sectioned views of bone fragments being held together with a twisted wire connection subject to breakage;

FIGS. 2, 2', 2a and 2b are are side views of radius cutters of the present invention and their utilization with respect to perpendicular and angled apertures made in the bone fragments;

FIGS. 3 and 3a are a side view of a second embodiment of a radius cutter of the present invention and its utilization in angled apertures in the bone fragments; and FIGS. 4, 4a and 4b are a side view of a third embodiment of a radius cutter of the present invention and its utilization with respect to perpendicular and angled apertures in said bone fragments.

Generally the present invention comprises a method for reducing the incidence of breakage of wires utilized in effecting connection of bone fragments during healing. The utilization of wires, in effecting such wire connection, has required the drilling of apertures in the cortex of the bone fragments. I have discovered that a primary cause of wire breakage in such wire connections is, in fact, the very use of such apertures. The edges of the apertures are brought into and remain in constant stressed contact with the tightened wire with occasional resultant breakage of the wire at such points. The method of the present invention comprises the elimination of such points of stress at the positions of said apertures which contact the wire of the wire connection. The points of stress are eliminated by shaping the contact edges of the apertures into a smoothly flowing curve with minimal or no residual bumps, ridges or edges and the like which may also function in causing stress raiser formation in the wire. The external edges of the apertures nearest the break or fracture line of the bone, i.e. the edges contacting the wire, are formed into a curve of at least about 90°, with the outer ends of the curve being smoothly blended into the outer surface of the bone. Such rounding should not however in itself result in bumps, edges and ridges being formed. It should be noted that an uncommonly formed aperture angled away from the break or fracture will require a curve having less than the aforementioned 90° curve to effect the requisite smooth curve formation.

With originally angled apertures, such cutting of about a 90° curve may result in a slight ridge formation at the point of intersection of the radius and the inner angled aperture wall. It is accordingly preferred that a further curve be formed to eliminate such ridge as well. Additionally, though the aperture edge facing the interior of the bone does not stress the wire to as great an extent as the outer edge thereof (since the interior bone surface is relatively soft) it is preferable that it also be eliminated by rounding thereof into a curve.

Though the method of the present invention may, in part, be effected by careful manipulation of the drill (utilized in initially making the aperture) as a file for rounding, it is nevertheless preferred that specific novel tools be utilized for such purpose. It may be specifically noted that rounding of the aperture edge of the inner cortex, when the bone fragments are fully apertured, is not in fact possible by utilization of the drill alone. A novel rotating radius cutter with a shank for engagement with a surgical drill and having one or more arcuate cutting blades (at least two are preferred for stability particularly with manual manipulation) with each having a subtended arc of 90° (deviations of up to about 20% may similarly provide results acceptable to varying degrees) is utilized in removing the stress raising corner of the outer aperture edge nearest the fracture site. The external curvature of the cutting blade preferably runs out into an external non-cutting flat surface, perpendicular to the axis of rotation of the radius cutter, which functions as a stop when the cutting with curve formation is properly complete. As a result only a smooth curve, without edges, is formed on the outer surface of the bone fragments with which the wire is in contact. Such radius cutter further embodies either an integral drilling member such as a fluted twist or pointed blade or other positioning means such as a blank drill or pilot. A radius cutter with the integral drill may be utilized in simultaneously forming the aperture and removing the stress raising corners. Alternatively such radius cutter with integral drill may be utilized for removing stress raising corners in previously formed apertures whether perpendicular or angled. In both instances the drill itself functions as positioning means for effective placement of the radius cutter. In either type of aperture the radius cutter with integral drill is perpendicularly inserted within the aperture to effect the properly rounded curvature. Angled apertures are at times utilized for facilitating wire insertion and positioning and such angles range between 30° to 90° and particularly between 45° to 60° from the horizontal, toward the fracture. In such apertures the radius cutter with integral drill generally causes the partial removal of, or drillng into the lower edge of the aperture, distal from the fracture, for proper positioning of the radius cutter. However such removal does not significantly affect the healing process. A radius cutter with a blank drill or pilot positioning means, preferably with a rounded end to facilitate aperture insertion, may be utilized for removing stress raising corners from predrilled perpendicular apertures. However, since it cannot remove said lower edge of the aperture, distal from the fracture, it cannot therefore readily be properly positioned. Accordingly such radius cutter with positioning means is not generally utilized with predrilled angled apertures.

Predrilled angled apertures present further problems where the 90° curve formed by the aforementioned radius cutter meets the angle of the inner wall of the aperture thereby forming a ridge. Accordingly, a radius cutter having an additional arc distance at its lower periphery adjacent the drilling member is preferably utilized to remove or prevent said ridge from being formed. Though such radius cutter may gouge the inner surface of the aperture since no stress raising edge is formed thereby, such gouging is not detrimental. In order to effect this aspect of the present invention it is preferred that the manipulation of such radius cutter be effected in conjunction with a jig for more precise operation. It is additionally preferred for facilitated handling that a small portion on the cutting blade between the two arc lengths be a non-cutting or dulled section which thereby functions as a lateral stop. Such portion may be part of a single arc or a slight area of arc separation.

Removal of the lower edge of the aperture nearest the line of fracture or, where applicable, the far outer cortex edge when the far cortex is also apertured, is optional. Such removal is accomplished by means of another embodiment of the radius cutter of the present invention. Such radius cutter comprises positioning means (which may embody a drill) and a cutting blade or blades positioned in the direction opposite to those of the radius cutters described above, i.e. towards the surgeon or operator of the radius cutter. The angle subtended by the arc of the cutting blade of such radius cutter is substantially equal to the angular deviation of the aperture from the horizontal, i.e. if not perpendicular, the acute angle formed with the surface of the bone. Such radius cutter is manipulated for operation by full insertion thereof within the aperture with lateral movement and reverse movement thereafter to bring the cutting blade or blades into contact with the lower edge of the aperture and for the rounding cutting thereof. Because of the equality of the angle of the aperture and the angle of the subtended arc of the cutting surface, completion of the rounding of the edge results in the full and automatic withdrawal of the radius cutter from the aperture. Such radius cutter is also utilized in conjunction with fully apertured bone fragments since the inner cortex surface, i.e. towards the body interior is generally inaccessible for rounding.

In preferred application relative to orthopaedic surgery, the aperture formed in the bone fragments is between 1/16" (1.59 mm) and 3/16" (4.76 mm) in diameter to readily accommodate the surgical wires used in such applications with diameters up to 0.040" to 0.062" (1.0 mm to 1.57 mm) or less and wire passers with diameters up to 3/16" (4.76 mm) or less. In such applications the length of the radius of the circles which define the curvature of the cutting blades as described below is between 1/64" to ⅜" (0.40 mm to 9.5 mm). The length of the drilling segment is up to about ½" (12.7 mm) with a length of between 1/16' to ⅜" (1.59 mm to 9.5 mm) being preferred and generally sufficient to penetrate the cortex of most of the bones in the human body but with a length of 3" to 4" (76.2 mm to 101.6 mm) used when penetration of the entire bone i.e. both cortices is desired. The length of the pilot positioning means is similarly between 1/16" to ⅜" (1.59 mm to 9.5 mm) with stability of the radius cutter being the requisite determinative criterion for the relative dimensions of length and diameter of the pilot positioning means. Alternatively, both the drilling segment and pilot positioning means may be separable members relative to the cutting blades with the lengths thereof being adjustably variable. For example such drilling segment or pilot positioning means may be positioned within an aperture centrally located on said cutting blades and held in position by a set screw. The positioning means in all of the embodiments is sized to allow for a snug but sliding fit within the apertures to restrict wobble during cutting but without causing binding during positioning or withdrawal of the radius cutter. With respect to the arc subtended by the various radius cutter embodiments there may be a deviation from the enumerated angles of approach by the operator up to about 20% without overly significant deterioration of the cutter performance.

With specific reference to the drawings, FIG. 1 depicts a typical twisted wire connection for holding bone fragments together during healing. As shown, fragments 2 and 3 of bone 1 are abutted together at the line of fracture 4. Angled apertures 8 and 9 are drilled into the cortex 7 of each of the bone fragments 2 and 3 respectively into the medullary canal 5 of the abutted bone fragments. Surgical wire 6 is drawn into one of apertures 8 or 9, through medullary canal 5 along the lower surface of the cortex 7, across the line of fracture 4 and out of the other aperture. (The fragments 2 and 3 may be fully apertured with the wire 6 being drawn across the outer surfaces of the bone fragments instead of through the medullary canal as shown in FIG. 1a.) The ends of wire 6 are gathered together and tightly twisted into helix 6' with the bone fragments 2 and 3 being held together thereby. With such tightening, the wire is brought into stressed contact with aperture edges 18 and 19 and the outer surface of bone fragments 2 and 3 between the apertures 8 and 9. The sharp edges such as aperture edges 18 and 19, particularly with angled apertures, tend to weaken the wire 6 with possible breakage thereof. To obviate such problem the aperturing drill may, during the formation of apertures 8 and 9, be withdrawn carefully while slowly rotating the drill toward the line of fracture to at least a perpendicular position. Aperture edges 18 and 19 may be therefore filed down by such action (with perpendicular apertures the drill is rotated towards the line of fracture to achieve a similar effect).

It is however preferred that, in effecting the removal of the stress producing edges, the novel radius cutting tools shown in FIGS. 2, 3 and 4 be utilized since such tools reduce the difficulty and skill required in removing such stress raising edges or corners. The radius cutter 20 in FIG. 2 comprises a shank 21 sized to fit within the chuck of a surgical drill (preferably a standard quarter inch (6.35 mm) diameter). The body 22 of radius cutter 20 comprises one or more (two or more being preferred for stability) cutting blades 25 having a curvature defined by circles 27 shown in dotted lines such that from line C—C (the line linking the centers,C, of circles 27) to the outer edges of the cutting blades 25 there is a 90° arc. The arc however runs out into a non-cutting flat section 26 at the very end of the cutting blade past the 90°, as shown, such that it functions as a stop for the radius cutter blades and is parallel to the line C—C. As a result, gouging, with ridge formation on the outer surface of bone fragments 2 and 3 which would tend to weaken wire 6 in contact therewith, does not occur. Such non-cutting flat section 26 may be an integral part of the cutting blade or more preferably is a ring section which additionally imparts mechanical strength and stability to the radius cutter or a combination of both.

Integral member 23 of radius cutter 20 may be a drilling member such as a pointed blade or a fluted twist drill (as shown) whereby the radius cutter 20 forms the required apertures while simultaneously removing the stress raising edges of the apertures on the outer surface of the bone. In such embodiment, particularly, the radius cutter is specifically adapted to effect a plunge cut in conjunction with the drilling of the aperture. Integral member 23 may alternatively be a non-drilling pilot such as member 23' in FIG. 2' for use as a positioning means for the radius cutter in pre-drilled apertures into which said pilot is sized to snugly fit. The radius cutter 20 with a drilling member, as shown, may be utilized in forming perpendicular apertures simultaneously with the removal of the stress raising aperture edge. It may also be utilized in removing the stress raising edges of angled pre-drilled apertures though it cannot be readily utilized in forming such angled apertures initially. The radius cutter with the non-drilling pilot, as a practical matter, is generally utilized in conjunction with pre-drilled perpendicular apertures since use with an angled aperture may result in undesired external removal of bone by the radius cutter.

When the radius cutter 20 is utilized in conjunction with bone fragments, the resultant aperture configuration is shown in FIGS. 2a and 2b. In FIG. 2a perpendicular apertures 8' and 9' (pre-drilled or formed by the radius cutter equipped with a drilling member) in bone fragments 2 and 3 respectively have stress raising edges 10 and 11 respectively. These edges are removed by the radius cutter 20, as indicated by the dotted lines with a smooth 90° curve being formed thereby on the outer peripheral edges of apertures 8' and 9' nearest the fracture line 4.

In utilizing the radius cutter 20 (having a drill member) with a pre-drilled angled aperture as in FIG. 2 b, the drill 23 is perpendicularly inserted. As a result, sections 12 and 13 of the aperture wall, distal from the fracture line, are of necessity drilled into. Such drilling is however not detrimental to the healing process. However, a small edge may be formed at points 14 and 16 where the radius blends into the angled wall portions, nearest the fracture, of apertures 8 and 9 respectively. In order to remove or prevent the occurrence of such edges, the radius cutter 30 in FIG. 3 may be utilized. Such radius cutter is utilized with pre-drilled angled apertures and is comprised of shank 31, body 32 with a cutting blade or blades 35 similar to that of the radius cutter 20 in FIG. 2. Such radius cutter 30 differs in that rather than a straight drill or pilot section 23 as in the radius cutter 20 of FIG. 2 there is a flared drill blade point 33 having an additional subtended arc beyond the 90° with a cutting blade 38 which extends beyond and below the centrally connecting line C—C' between the center of circles 37 which define the original arc of cutting blades 35. As in the radius cutter 20 there is a similar non-cutting flat surface 36 to similarly act as a stop for the radius cutter and to prevent ridges formed by gouging. The additional arc of the cutting blade removes edges 14 and 16 such as is formed with the radius cutter 20 in FIG. 2. As shown in FIG. 3a radius cutter 30 rounds edges 14 and 16 and may cause non-stressing depressions 15 and 17 on the interior wall surface of apertures 8 and 9 respectively. More preferably angle $\alpha$ of the apertures is substantially matched with the additional subtended arc of angle $\alpha$ of blade 38 to remove edges 14 and 16 without any formation of depressions. In any event, for ensured effectiveness the angle subtended is at least equal to said angle $\alpha$. As with radius cutter 20, radius cutter 30 similarly may remove part of sections 12' and 13' respectively of the aperture walls distal from the fracture site but again without substantial ill effect. To ensure precise handling of such cutter in removing edges 14 and 16 it is preferred that radius cutter 30 be utilized with a jig positioned on the outer surface of the bone. Alternatively, dulled section 34 functions as a lateral stop to ensure precise removal of said edges 14 and 16 without excessive accidental bone gouging.

The utilization of the radius cutters 20 and 30 in FIGS. 2 and 3 does not eliminate the interior aperture edges. However such edges are generally softer and do not present as great a problem with respect to wire breakage. However, if desired, such interior aperture edges may be removed by radius cutter 40 shown in FIG. 4. Radius cutter 40 in contrast to the radius cutter 20 and 30 of FIGS. 2 and 3 has an upward cutting edge 45 at the end of shank 41. The curvature of cutting edge 45 is determined by circles 47 with the arc thereof ranging from the outer edge 46 to the line C—C'' connecting the centers of circles 47. The arc subtended $\beta$ is predetermined as being substantially equal to the angular deviation $\beta$ of the pre-drilled aperture from the horizontal. Body member 42 of radius cutter 40 (which may be ring shaped) is sized to snugly but slidingly fit within predrilled apertures. Upon full insertion within the pre-drilled apertures, radius cutter 40 is moved laterally to engagement of cutting blade 45 with the lower aperture edges proximal to the fracture line. Upon such engagement the radius cutter is slowly pulled outwardly with complete rounding of the edge, this rounding allows the radius cutter to be pulled out of the aperture with ease. Outer edge 46 of blade 45 is rounded to prevent unnecessary gouging of the bone and to further facilitate removal of such radius cutter 40 by providing a gliding-rolling, or sliding surface. Segment 43 may be a drilling member if desired, particularly if the bone fragments are fully apertured such as shown in FIG. 1a. With such utilization such radius cutter 40 serves to round the outer surface of the inner cortex, facing the body interior, at the edge of the apertures wherein a drill or the radius cutters 20 and 30 cannot so function. FIGS. 4a and 4b illustrate the removal of inner aperture segments 44 and 48 and 44' and 48' respectivley from the aperture walls nearest the fracture line 4 from both perpendicular and angled apertures 8' and 9' and 8 and 9 respectively.

With the utilization of the above described radius cutters removal of some or all of the stress raising areas formed by the drilling of apertures may be effected. It is understood that the above description and specific configurations of radius cutters and dimensions and uses thereof are illustrative of the present invention and are not to be construed as limitations on the present invention. Changes in structure, configuration, dimensions, applications and the like may be made without departing from the scope of the present invention as defined in the following claims. For example while the utilization of the radius cutters and method of the present invention have been specifically described with respect to orthopaedic surgery they may be utilized with similar effect in other surgical applications relating to holding hard surfaced materials such as bones or teeth together. These applications include maxillo-facial surgery, spinal surgery, scoliosis surgery, neuro-surgery, and thoracic and caridothoracic surgery with respect to the closing of the sternum after open heart surgery as well as other applications requiring knitting and/or proper positioning of bones. Dental surgery and orthodontics which involve wire connections are similarly included with teeth, particularly having dead nerves therein, being functionally equivalent to the bone fragments described above. Accordingly, for the purpose of describing the present invention teeth will be referred to as bones herein. With respect to dentistry it is further noted that the radius cutter 30 in FIG. 3 may also be utilized in drilling teeth for the locking insertion of an amalgam filling. Additionally the novel radius cutters of the present invention are applicable and utilizable with respect to general tool utilization whenever there is a requirement for the removal of stress raising edges.

What is claimed is:

1. A rotating radius cutter means forming a radius to remove stress raising corners of an aperture formed in a bone fragment for passing a wire therethrough in the formation of a wire connection between bone fragments, said radius cutter means comprising a blade having a subtended arc of an angle of at least about 90°, with said blade being adapted to cuttingly engage said external stress raising corners of said aperture to effect such removal with the formation of a curve from the interior of said aperture to the outer surface of said bone fragment, wherein said blade, at the outer periphery thereof, which engages said outer surface, has a non-cutting flat surface for a distance sufficient to prevent gouging of the outer surface of said bone by said blade, and wherein said radius cutter means further embodies positioning means, for properly positioning said blade for effecting said removal, comprising a non-cutting pilot sized to snugly fit within said aperture.

2. A rotating radius cutter means forming a radius to remove stress raising corners of an aperture formed in a bone fragment for passing a wire therethrough in the formation of a wire connection between bone fragments, said radius cutter means comprising a blade having a subtended arc of an angle of about 90°, with said blade being adapted to cuttingly engage said external stress raising corners of said aperture to effect such removal with the formation of a curve from the interior of said aperture to the outer surface of said bone fragment, wherein said blade, at the outer periphery thereof, which engages said outer surface, has a non-cutting flat surface for a distance sufficient to prevent gouging of the outer surface of said bone by said blade, and wherein said radius cutter means further embodies positioning means, for properly positioning said blade for effecting said removal, comprising a cutting drill member.

3. A rotating radius cutter means forming a radius to remove stress raising corners of an aperture formed in a bone fragment for passing a wire therethrough in the formation of a wire connection between bone fragments, said radius cutter means comprising a blade having a subtended arc of an angle which exceeds 90° by an angle at least equal to the acute angle of deviation of said aperture from the horizontal relative to the surface of said bone fragment, with said blade being adapted to cuttingly engage said external stress raising corners of said aperture to effect such removal with the formation of a curve from the interior of said aperture to the outer surface of said bone fragment, wherein said blade, at the outer periphery thereof, which engages said outer surface, has a non-cutting flat surface for a distance sufficient to prevent gouging of the outer surface of said bone by said blade, and wherein said radius cutter means further embodies positioning means, for properly positioning said blade for effecting said removal, comprising a cutting drill member.

4. The radius cutter means of claim 3 wherein a small segment on said cutting blade, between said 90° and the subtended arc of the angle which exceeds said 90°, is of reduced cutting ability whereby it is capable of functioning as a lateral stop against the interior wall of said aperture.

5. A rotating radius cutter for substantially removing the edges of an angled aperture made in adjacent portions of the proximal cortical wall of abutting bone fragments for permitting the passage of a wire therethrough in the formation of a wire connection between said bone fragments, said edges being in stressed contact with said wire and on the inner cortical surface of said bone fragments, wherein said radius cutter comprises positioning means sized to snugly fit within said aperture and a radius cutting blade adapted to cuttingly engage said aperture edges proximal to the fracture line between said bone fragments to effect such removal with the formation of a curve from the inner cortical surface of said bone fragment to the inner wall of said aperture with said cutting blade having a subtended arc substantially equal to the acute angle of deviation of said aperture from the horizontal relative to said bone surface, and wherein said cutting blade is located between said positioning means and a drive shaft having a diameter less than that of said positioning means.

6. The radius cutter of claim 5 wherein the outer portion of said cutting blade is rounded.

7. The radius cutter of claim 5 wherein said positioning means comprises a cutting member which initially forms said aperture.

8. A rotating radius cutter for substantially removing the edges of an angled aperture made in a bone fragment with said aperture passing through the diameter of said bone fragment and being made for permitting the passage of a wire therethrough in the formation of a wire connection between bone fragments, said edges being in stressed contact with said wire and on the outer surface of said bone fragment contiguous to said wire connection, wherein said radius cutter comprises positioning means sized to snugly fit within said aperture and a radius cutting blade adapted to cuttingly engage said aperture edges proximal to the fracture line between said bone fragments to effect such removal with the formation of a curve from said outer surface of said bone fragment to the inner wall of said aperture with said cutting blade having a subtended arc substantially equal to the acute angle of deviation of said aperture from the horizonatal relative to said bone surface, and wherein said cutting blade is located between said positioning means and a drive shaft having a diameter less than that of said positioning means.

9. The radius cutter of claim 8 wherein the outer portion of said cutting blade is rounded.

10. The radius cutter of claim 8 wherein said positioning means comprises a cutting member which initially forms said aperture.

* * * * *